United States Patent [19]
Huffstutler, Jr. et al.

[11] 4,240,161
[45] Dec. 23, 1980

[54] ARCUATE DISC HEART VALVE

[75] Inventors: Miles C. Huffstutler, Jr., Burnsville; Marshall S. Kriesel, St. Paul; Lawrence Anderson, Fridley, all of Minn.

[73] Assignee: Medical, Incorporated, Inver Grove Heights, Minn.

[21] Appl. No.: 13,375

[22] Filed: Feb. 21, 1979

Related U.S. Application Data

[63] Continuation-in-part of Ser. No. 821,400, Aug. 3, 1977, abandoned.

[51] Int. Cl.³ .................................................. A61F 1/22
[52] U.S. Cl. ...................................... 3/1.5; 137/527.8
[58] Field of Search .................. 3/1.5; 137/527, 527.8

[56] References Cited

U.S. PATENT DOCUMENTS

| | | | |
|---|---|---|---|
| 3,835,475 | 9/1974 | Child | 3/1.5 |
| 3,859,668 | 1/1975 | Anderson | 3/1.5 |
| 3,926,215 | 12/1975 | Macleod | 3/1.5 X |
| 4,057,857 | 11/1977 | Fettel | 3/1.5 |

*Primary Examiner*—Ronald L. Frinks

[57] ABSTRACT

A free floating pivoting disc heart valve in which the disc has a generally arcuate segment configuration positioned so as to present a generally convex surface toward the outflow side of said base and a generally concave surface toward the inflow side of the base when viewed in the closed configuration.

6 Claims, 14 Drawing Figures

ARCUATE DISC HEART VALVE

This application is a continuation-in-part of application Ser. No. 821,400 filed Aug. 3, 1977, now abandoned.

Previously considerable difficulty had been experienced in prosthetic heart valves including incomplete opening of the valve, excessive pressure losses across the valve, and excessive back flow through the valve during the closing phase.

These and other difficulties in the prior art have been overcome according to the present invention in which a generally arcuate segment configured disc is mounted within a base so that the disc pivots generally chordally of the passage through the base. The disc is allowed to float freely so that it moves responsive to the flow of fluid through the valve and is free to rotate about its own axis of rotation, yet is restrained in an operative position within the passage. The disc has a generally arcuate segment configuration. The downstream or outflow side of the disc has a generally convex surface. The convexity of the surface of the disc on the outflow side has been found to reduce pressure losses across the valve and to provide complete opening of the valve as compared to valves with planar discs. The upstream or inflow side of the disc has a generally concave surface. The concavity of the disc increases the opening rate of the valve as compared to flat and biconvex disc valves.

The convex-concave disc causes only a very small pressure drop across the valve during the opening phase and particularly in the last 5 to 10 degrees of travel during the opening phase. The arcuate disc moves very rapidly during the opening phase, particularly at the initiation and the ending of that phase. The arcuate disc requires only a small pressure gradient to initiate and sustain the opening phase. As a result the convex-concave disc permits a larger stroke volume with less heart work and causes less damage to the blood tissue. The disc moves to the full open position so that the pressure drop across the disc is minimized. Full and efficient washing of the disc is achieved. The requirement for a small pressure gradient to initiate and sustain the opening phase is particularly significant in the immediately postoperative period. Regurgitation during the closing phase is minimized because only very small pressure gradients are required to accomplish closing.

Pivoting disc heart valves in which the disc pivots chordally of the generally annular opening in the base so that the disc in the open position projects both above and below the plane of the valve base have generally previously employed configurations in which the disc had either a planar configuration or a generally biconvex configuration. The discs, according to the present invention, have a generally convex-concave configuration so that they form a shell or cap.

Free floating pivoting disc valves generally pivot around a chordal area which is offset from a diameter of the annular passage through the valve base. This lateral offset or eccentricity is necessary in order to provide an imbalance of forces on the disc which will permit the flow of fluid to pivot the disc about its chordal pivoting areas between the open and closed positions. The rate of opening and closing decreases as the eccentricity decreases. As the chordal pivoting areas approach the diameter, the rate of opening and closing of the disc becomes unacceptably low. The pressures required to cause the initiation and continuation of the opening and closing movements of the valve discs are also decreased as the eccentricity is decreased. The lowering of the required opening and closing pressures is very desirable; however, decreasing the eccentricity so as to achieve the lowest possible pressures results in unacceptably slow opening and closing rates. The use of a convex-concave disc permits the eccentricity to be reduced to very low values while maintaining acceptably rapid rates of opening and closing.

The use of chordal pivoting areas which are offset only slightly from the diameter of the generally annular passage through the valve base also allows more equal flow of blood on each side of the valve disc in the open configuration. This provides good washing on both sides of the disc and permits the formation of approximately symmetrical vortices downstream from the valve. Where there is a small flow on one side of the disc and a dispropotionately larger flow on the other side of the disc, the vortices which are formed downstream from the valve are asymmetrical. It requires more work from the heart to pump blood through a system in which asymmetrical vortices are formed than it does through a system where symmetrical vortices are formed.

The pivoting disc pivots about a small chordal area in such a way that the instantaneous pivotal axis shifts through an area as the disc moves between the open and closed positions. Preferably, the concavity of the pivoting disc is great enough so that, at least in the central area of the disc, the instantaneous pivot axes do not pass through the body of the disc. In the central area of the disc the pivot axes preferably pass on the downstream or inflow side of the concave surface of the disc. In this preferred configuration the center of pressure of the blood acting on the disc during the opening phase of the valve's operation shifts so as to increase the length of the lever arm between the center of pressure and the instantaneous pivot axes as the disc pivots through the opening phase. Where the disc is restrained in the valve base so that it pivots about one set of pivot projections during the opening phase and a second set during the closing phase, the instantaneous pivot axes which are generated as the disc pivots or rolls around the opening pivot projections generally pass closer to the concave surface of the disc than do those generated during the closing phase.

The concave and convex surfaces of the free floating discs according to the present invention do not necessarily define smooth arcs. The free floating disc has a generally arcuate segment configuration which includes a circular base plane. The circumference of the base plane is defined by the line which is formed when the disc is placed on a planar surface with its concave side towards that surface. The edge of the disc makes contact with the planar surface along a circle which extends entirely around the edge of the disc. This circle defines the circumference of the base plane for the arcuate segment. The height of the convex surface of the disc is measured along the axis of rotation of the disc from the location where that axis of rotation pierces the base plane to the location where it pierces the surface of the disc on the convex side. The height of the concave surface is measured along the axis of rotation from the point where it pierces the base plane to the point where it pierces the surface of the disc on the concave side. The concavity of the disc is defined as the height of the concave side divided by the diameter of the base. The convexity of the disc is defined as the height of the convex surface divided by the diameter of the base. The nominal radius of the concave side is that radius which defines a smooth circular arc which includes both ends of a diameter of the base and the point where the axes of rotation pierces the concave surface. Likewise the nominal radius of the convex side is that radius which defines a smooth circular arc which includes both ends of a diameter of the base and the point where the axes of rotation pierces the convex surface.

Most free floating disc heart valves are restrained for pivotal movement in such a way that they do not pivot about a single axis. There may be substantial lateral shift of the instantaneous pivot axes during one or both of the opening and closing phases and often the character of the pivotal movement during one of the phases is quite different during the other of the phases. Eccentricity is a measure of the lateral offset from the instantaneous pivot axes to the axes of rotation. The eccentricity is defined as the amount of the lateral offset divided by the diameter of the base plane. The eccentricity for the opening phase is determined by measuring the lateral offset between the axes of rotation and the instantaneous pivot axis at the initiation of the opening phase. The lateral offset is measured parallel to the base plane and normal to the initial opening phase instantaneous pivot axis. The eccentricity for the closing phase is determined by dividing the lateral offset between the initial closing phase instantaneous pivot axis and the axis of rotation by the diameter of the base plane.

In order to achieve the advantages of the present invention the opening phase eccentricity of the disc should be from about 0.05 to 0.20 and preferably approximately 0.17. The convexity should be from about 0.05 to 0.20 and preferably from about 0.10 to 0.15. The concavity should be such that at least some if not all of the opening phase instantaneous pivot axes pass in the central region of the disc through empty space on the inflow side of the concave surface. The concavity generally ranges from about 0.05 to 0.10.

The structure used to restrain the pivoting free floating disc may restrain the disc by peripheral contact or by engaging with some feature on a surface of the disc. In general, the disc should be restrained so that it is not permitted to open to an angle greater than from about 75 to 80 degrees and perferably about 80 degrees. The opening angle is determined by measuring the angle between the longitudinal axis of the valve and the axis of rotation of the disc. The disc in the closed position generally rests at an angle from about 1 to 25 degrees, and preferably approximately 12 degrees. The closed angle should be as small as possible so as to reduce the height of the valve base. Reducing the height of the valve base reduces the mass of the valve as well as the turbulence generated by the constricted flow of blood through the valve.

Referring particular to the drawings which are submitted for purposes of illustration and not limitation, there is illustrated:

Figure 1:
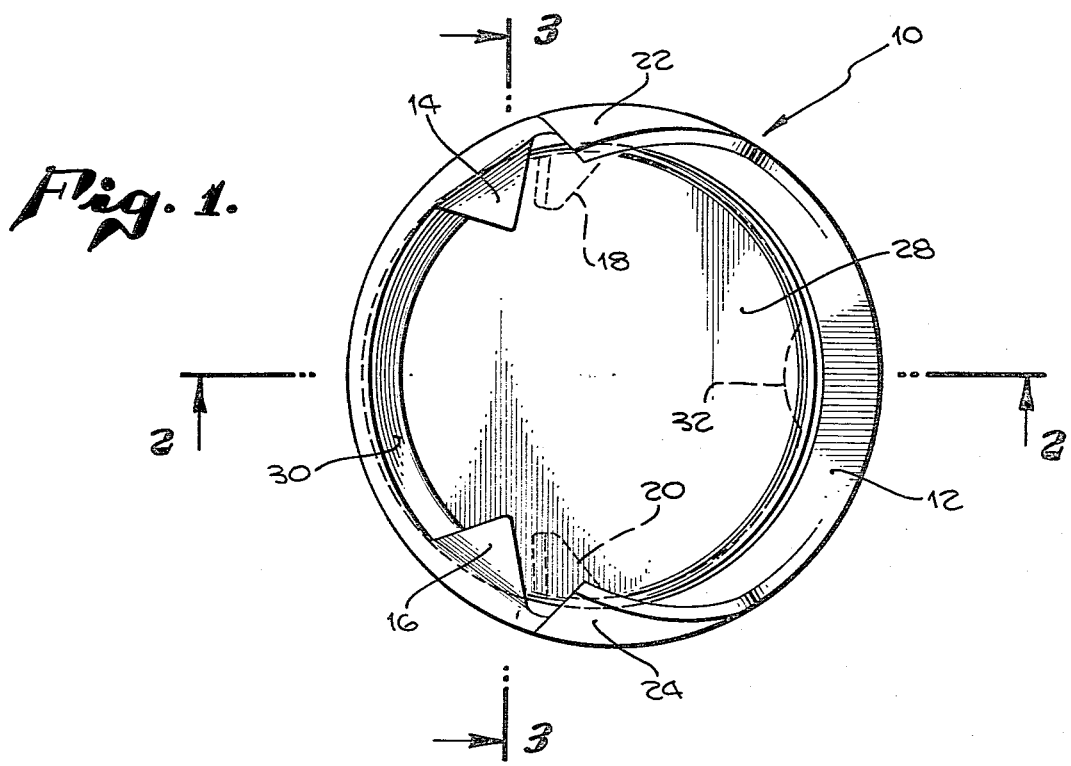
FIG. 1 is a plan view of a free floating pivotal disc heart valve which incorporates an arcuate segment disc of the present invention.
Figure 2:
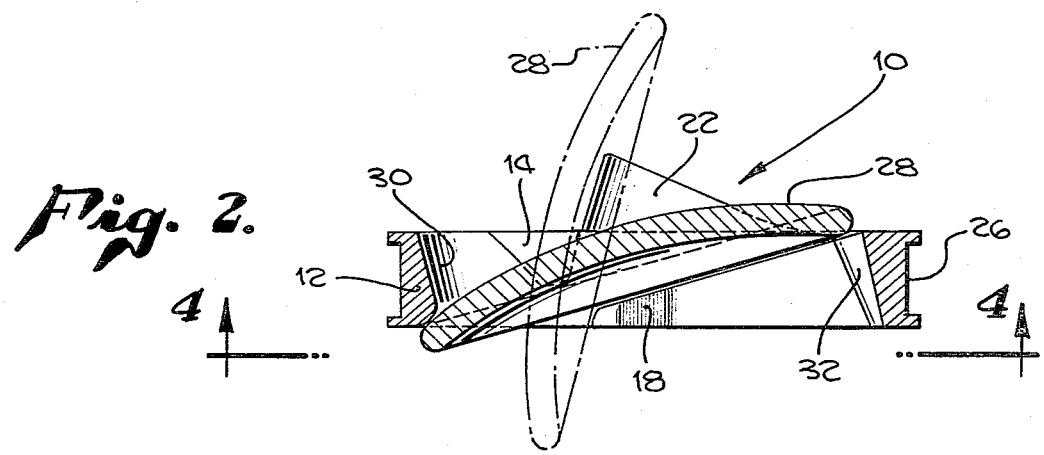
FIG. 2 is a cross-sectional view taken along line 2—2 in FIG. 1.
Figure 3:
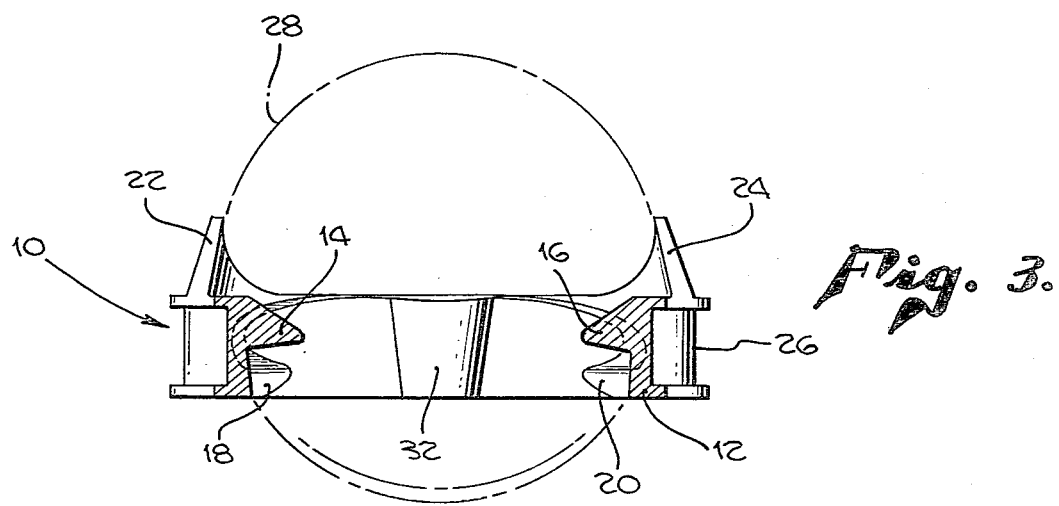
FIG. 3 is a cross-sectional view taken along line 3—3 in FIG. 1.
Figure 4:
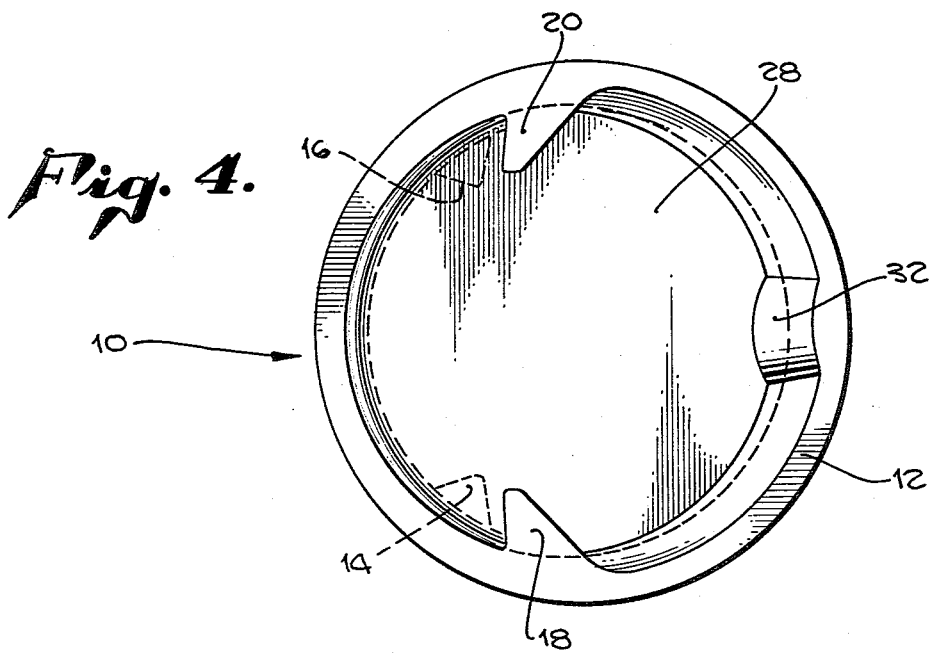
FIG. 4 is a bottom view partially in cross-section taken along line 4—4 in FIG. 2.

Referring particularly to the drawings, there is illustrated particularly in FIGS. 1 through 4 a pivoting disc free floating heart valve in which the disc pivots within the flow passage of the valve indicated generally at 10. The valve includes a base 12. Integral with the base 12 are opening pivots 14 and 16, closing pivots 18 and 20, and disc retainers 22 and 24. A suture ring retainer groove 26 is provided on the exterior of the valve base so as to permit attachment of a suturing ring, not shown. A disc 28 is retained in operative relationship with base 12 so that it opens and closes responsive to the flow of fluid through the valve 10. The blood flows through generally annular passage 30 in one direction. Disc 28 pivots freely under the force of forward flowing blood to open the valve so as to permit blood to flow therethrough. As soon as blood begins to flow in the reverse direction through the valve, it carries disc 28 with it so as to close the valve and prevent the flow of blood therethrough. A disc stop 32 is provided to insure that the disc rests in the desired location in the closed configuration and does not pivot too far in the closing phase. The valve is constructed of rigid antithrombic materials, such as titanium and carbon. The nature of the materials and the design and configuration of the device are such that a perfect seal is not generally achieved, and there is some weeping around the edges of the disc in the closed position. The volume of regurgitation through the valve in the closed configuration is controlled so that it does not significantly increase the amount of work required by the heart.

The size of the opening and closing pivots and the disc retainers has been shown enlarged in proportion to the base for the purposes of simplifying illustration of the device. During the opening phase of the valve's action, the disc pivots around opening pivots 14 and 16 between the closed and opened positions, as illustrated particularly in FIG. 2. During the closing phase the disc 28 pivots about the closing pivots 18 and 20. The disc is retained in an operative position during the opening phase and while in the open configuration by disc retainers 22 and 24. The disc is retained in operative position during the closing phase by contact between the periphery of the disc 28 and the wall between the opening and closing pivots. The edge of the disc contacts the wall between pivots 14 and 18 on one side and 16 and 20 on the other side of base 12 and remains in contact with this area as it pivots through the closing phase. Slight lateral movement of the disc is permitted during the opening and closing phases so as to permit the disc to move freely. The disc rotates about its own axes of rotation during operation so as to distribute wear and avoid the formation of thrombus.

The concave-convex nature of the flow actuated disc or occluder 28, in addition to the advantages discussed elsewhere herein, acts to cause the valve to open fully during the opening phase. It is believed that particularly with planar discs the valve fails to open fully in some isolated instances. There is some indication that this incomplete opening may be due to a boundary wall or Coanda effect. Although this invention is not limited to any theory, it is believed that the convex-concave disc 28 acts to cause an anticoanda effect.

In general, heart valve prosthesis are used most commonly in the mitral and aortic positions. The inherent differences between the functions required of the aortic and mitral valves indicates that there may be some differences in the optimum valve designs for these two positions.

Figure 5:
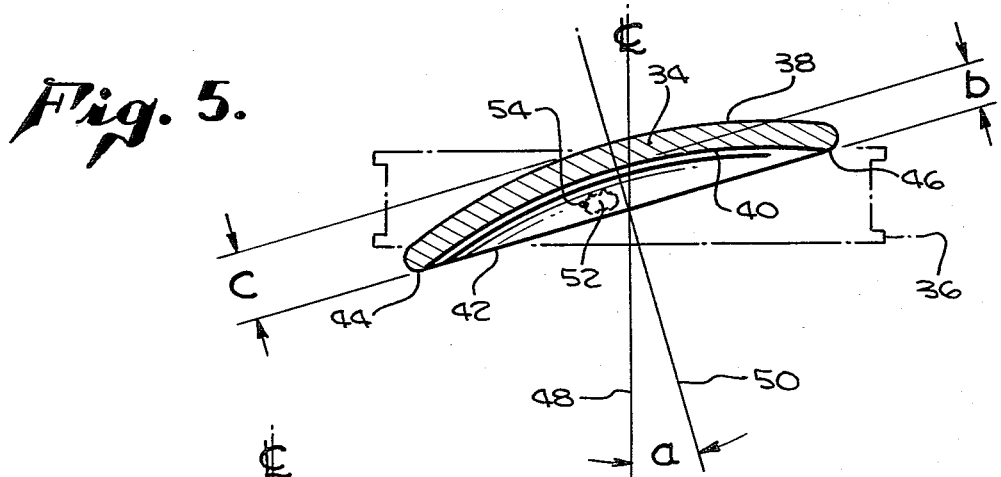
FIG. 5 is a schematic illustration of a valve of the present invention in the closed configuration.
Figure 6:
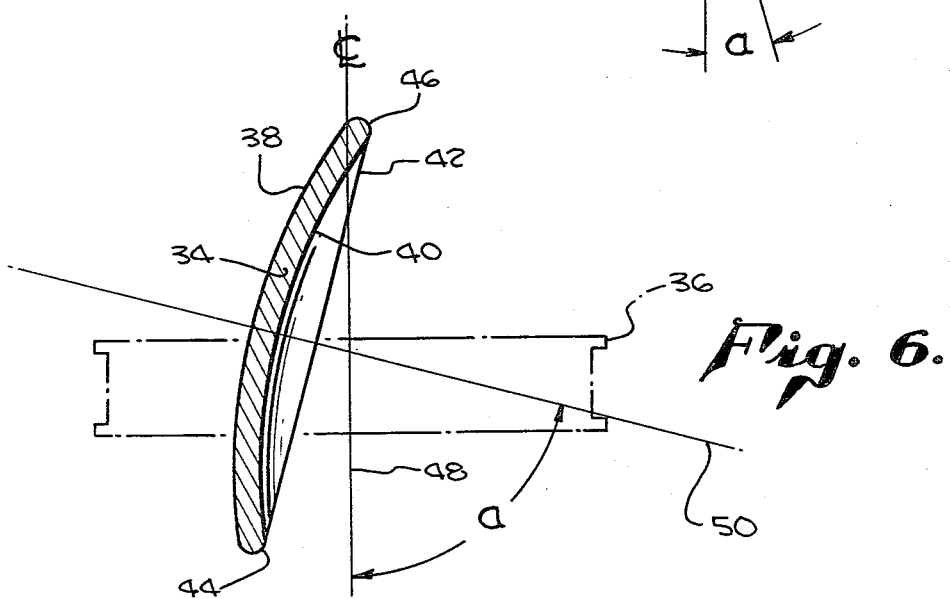
FIG. 6 is a schematic illustration similar to FIG. 5 showing the valve in the full open position.

Throughout FIGS. 5 through 14 the height of the concave surface is indicated as height b and the height of the convex surface is by the height c. In FIGS. 5 and 6 the angle a is the angle between the center line of the valve and the axes of revolution of the disc.

Referring particularly to FIGS. 5 and 6 there is a diagrammatic illustration of a valve according to the present invention in which an arcuate segment disc 34 is mounted for free floating pivotal movement within a base 36. The disc 34 has an arcuate convex surface 38 and an arcuate concave surface 40. The disc 34 has a geometric base 42. Base 42 is circular and the opposite ends of a diameter of geometric base 42 are indicated respectively at 44 and 46. The center line of the valve is indicated at 48, and the axes of rotation of disc 34 is indicated at 50. In FIG. 5 the angle a indicates the angle at which the disc 34 rests in the closed configuration. The angle a in FIG. 6 indicates the maximum opening angle of the valve when the disc 34 is in the full open configuration. The height b of the concave surface is the distance from the location where the axis of rotation 50 pierces geometric base 42 to the point where the axes of rotation 50 pierces concave surface 40. The height c of the convex surface 38 is the distance between the point where the axis of rotation 50 pierces the geometric base 42 and the point where it pierces the convex surface 38. Disc 34 is a spherical segment or cap. Disc 34 pivots chordally of base 36 through a chordal area 52, the approximate boundaries of which are indicated by an irregular area. The initial opening pivot axis 54 is offset from the axis of rotation 50. The eccentricity of the opening phase is determined by comparing the distance between initial opening pivot axis 54 and the axis of rotation 50 with the diameter of base 42.

Figure 7:
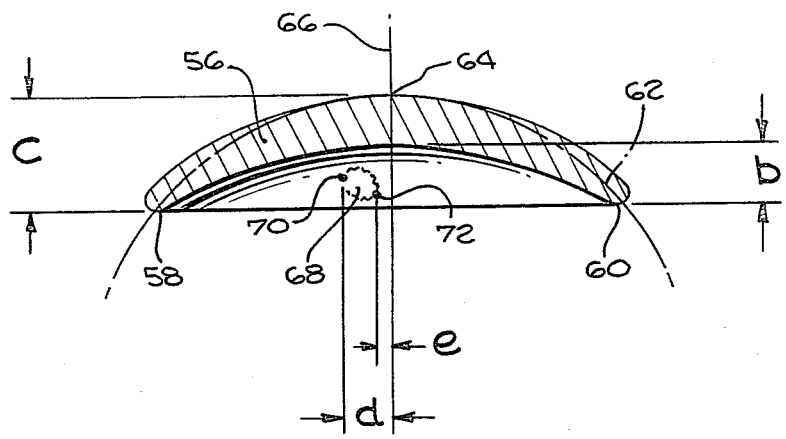
FIG. 7 is a cross-sectional view of a further embodiment of the generally arcuate segment disc of the present invention in which the disc is thicker in the center than at the edge.

Referring particularly to FIG. 7 there is illustrated in cross section a further embodiment in which the disc 56 has a convex-concave configuration in which the center of the disc is thicker than the periphery. The respective opposite ends of a diameter of the geometric base of disc 56 are indicated at 58 and 60. The nominal radius of the convex surface of disc 56 generates an arc indicated at 62. Sixty-two is a smooth constant radius arc which intersects both ends 58 and 60 of a diameter of the geometric base, and the point 64 at which the axis of rotation 66 intersects the convex surface of disc 56. The arc of the nominal radius of the concave surface is coextensive with the surface itself. The chordal pivot area 68 includes initial opening pivot axis 70 and initial closing pivot axis 72. The opening phase eccentricity offset is indicated at d and the initial closing phase eccentricity offset is indicated at e.

Figure 8:
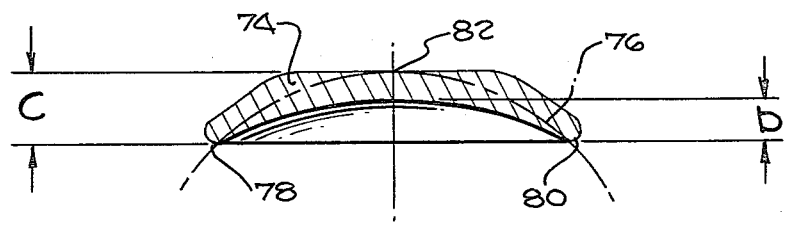
FIG. 8 is a further embodiment in which the central area of the convex side of the disc is defined by a plane.

Referring particularly to FIG. 8 there is illustrated a further embodiment in which the disc 74 has a convex surface which includes a peripheral arcuate portion and a generally planar central area. The nominal radius 76 of the convex side defines an arc of continuous radius which includes the end points 78 and 80 of a diameter of the geometric base of disc 74 and the point 82 at which the axis of rotation of disc 74 intersects the generally convex surface.

Figure 9:
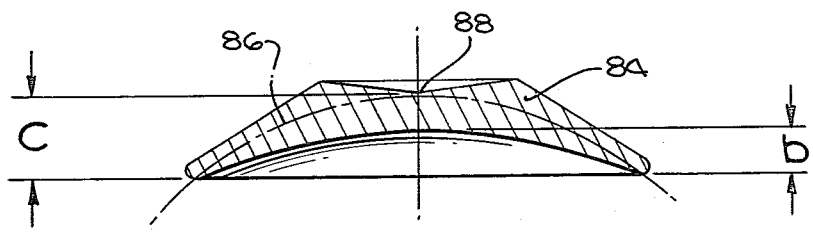
FIG. 9 is a further embodiment in which the central area of the convex surface of the disc is defined by a shallow conical depression.

Referring particularly to FIG. 9 there is illustrated an embodiment in which the convex surface includes a conical depression in the central area and generally conical peripheral areas. The nominal radius arc 86 of the convex surface of disc 84 includes the end points of the diameter of the geometric base of disc 84 and the point where the axis of rotation of the disc intersects the convex surface at 88.

Figure 10:
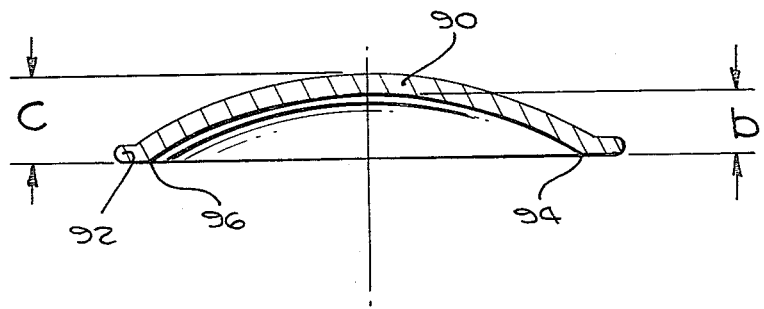
FIG. 10 is a further embodiment in which the edge of the disc defines a laterally projecting rim.

Referring particularly to FIG. 10 there is illustrated a disc 90 which is provided with a laterally projecting flange 92 at the periphery thereof. Flange 92 assists disc 90 in rapidly opening and closing and in achieving and maintaining its maximum design opening angle. The nominal radius of the convex surface of disc 90 is that which produces an arc which includes the opposite end points 94 and 96 of the geometric base of disc 90 and the point where the axis of revolution pierces the convex surface. The nominal radius of the convex surface is one which defines an arc which includes end points 94 and 96 and the point where the axis of revolution pierces the concave surface of the disc 90.

Figure 11:
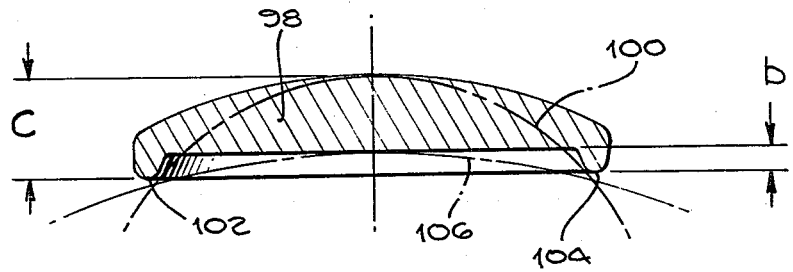
FIG. 11 is a further embodiment in which the concave side is formed by a generally annular peripheral rim and a central planar surface.

Referring particularly to FIG. 11 there is illustrated a disc 98 in which the concavity is defined by an annularly positioned axially projecting ring and a generally planar central surface. The arc 100 defined by the nominal radius of the convex side of disc 98 includes end points 102 and 104 and the point where the axis of rotation pierces the surface on the convex side of disc 98. The arc 106 is defined by the nominal radius of the concave side of the disc 98. Arc 106 includes the point where the axis of rotation pierces the concave side of the disc and the two end points 102 and 104 of the geometric base of disc 98.

Figure 12:
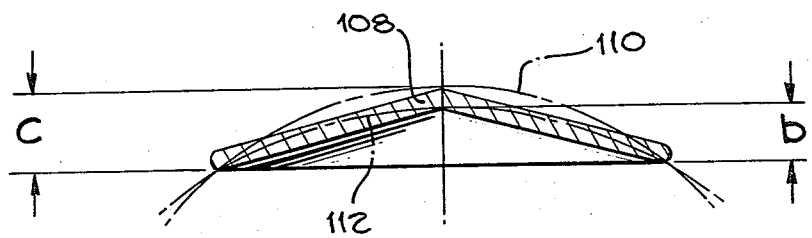
FIG. 12 is a further embodiment in which the convex and concave surfaces are conical.

Referring particularly to FIG. 12 there is illustrated a disc 108 in which the arc 110, which is defined by the nominal radius of the convex side of the disc, includes the apex of the conical surface on the convex side of the disc and the end points of the diameter of the geometric base of the disc. The arc 112 is defined by the nominal radius of the concave side of disc 108. Arc 112 includes the apex of the conical surface which is the concave side of disc 108 and the two end points of a diameter of the geometric base of disc 108.

Figure 13:
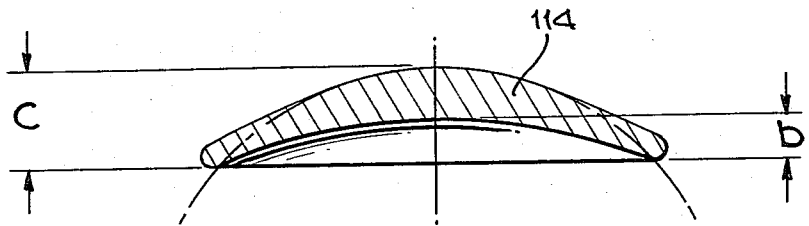
FIG. 13 is a further embodiment in which the convex surface is a generally truncated cone in which the cone is truncated with an arcuate surface.

Referring particularly to FIG. 13 there is illustrated a disc 114 in which the convex surface includes an outer conical surface which is truncated with an arcuate surface.

Figure 14:
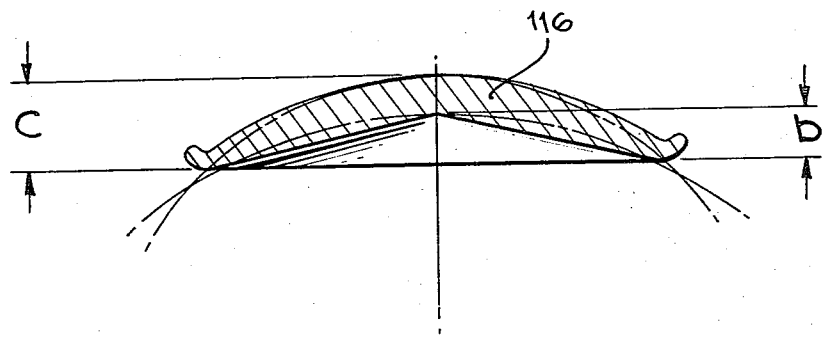
FIG. 14 is an additional embodiment in which the concave surface is conical, and an annular up-turned peripheral rim is provided on the disc.

Referring particularly to FIG. 14 there is illustrated an embodiment in which an up-turned annular peripheral flange is provided on disc 116. This flange assists blood moving through the valve to open and close the valve rapidly and to maintain it in full open position during the open phase of the valve's operation.

The disc in a typical aortic valve according to the present invention has a closed angle of about 12 degrees, an open angle of about 78 degrees, a geometric base diameter of about 21 millimeters, a spherical segment form with a constant thickness, an opening eccentricity of about 0.17, a concavity ranging from about 0.05 to about 0.10, and a convexity of from about 0.10 to 0.15.

What has been described are preferred embodiments in which modifications and changes may be made without departing from the spirit and scope of the accompanying claims.

What is claimed is:

1. A heart valve comprising:
    a base having a flow passage therein, said flow passage having an upstream side and a downstream side;
    a free floating flow actuated disc having a generally convex downstream side and a generally concave upstream side, means for confining said disc in said passage for rotation about its own axis of revolution and for pivotal movement about a plurality of instantaneous chrodal axes from a closed position through an opening phase to an open position and from said open position through a closing phase to said closed position, the initial instantaneous pivot axis having said opening phase being offset laterally from said axis of revolution, said disc having a circular geometric base, said offset being equal to from about 0.05 to 0.20 the length of a diameter of said circular geometric base, the height of said generally concave upstream side being equal to from about 0.05 to 0.10 the length of said diameter, and said initial instantaneous pivot axis extending for a part of its length on the upstream side of said generally concave upstream side.

2. A heart valve of claim 1 wherein said free floating disc has a generally hollow spherical segment configuration.

3. A heart valve of claim 1 wherein said instantaneous axes extend for a part of their length on the upstream side of said generally concave upstream side.

4. A heart valve of claim 1 wherein said disc has a circular geometric base, the height of said generally convex downstream side being equal to from about 0.10 to 0.15 the length of a diameter of said circular geometric base.

5. A heart valve of claim 1 wherein said disc opens to an angle of about 80 degrees.

6. A heart valve comprising:
    a base having a flow passage therein, said flow passage having an inflow side and an outflow side;
    an occluder having a generally convex-concave spherical segment configuration;
    means on said base contacting only the periphery of said occluder for confining said occluder for pivotal and rotational movement within said flow passage whereby said occluder pivots about a plurality of instantaneous chordal axes from a closed position through an opening phase to an open position responsive to the flow of fluid in a forward direction through said flow passage and from said open position through a closing phase to said closed position responsive to the flow of fluid in a reverse direction through said flow passage, said occluder being free to rotate about its own axis of revolution, said occluder being positioned when in said open position to permit fluid to flow in said forward direction on both sides of said occluder, the convex side of said occluder being on the outflow side of said flow passage, said occluder being at an angle of from about 1 to 25 degrees in said closed position and from about 75 to 80 degrees in said open position, at least some of said instantaneous axes extending for a part of their length during said opening phase on the inflow side of the concave side of said occluder, the initial instantaneous pivot axis during said opening phase being offset laterally from said axis of revolution, said disc having a circular geometric base, said offset being equal to from about 0.05 to 0.20 the length of the diameter of said circular geometric base.

* * * * *